(12) United States Patent
Gandhi et al.

(10) Patent No.: US 9,801,821 B2
(45) Date of Patent: Oct. 31, 2017

(54) STABILIZED VITAMIN D FORMULATIONS

(71) Applicant: PSM HEALTHCARE LIMITED, Manukau, Auckland (NZ)

(72) Inventors: Anilkumar S. Gandhi, Mumbai (IN); Pratibha S. Pilgaonkar, Mumbai (IN); Maharukh T. Rustomjee, Mumbai (IN)

(73) Assignee: PSM Healthcare Limited, Manukau, Auckland (NZ)

( * ) Notice: Subject to any disclaimer, the term of this patent is extended or adjusted under 35 U.S.C. 154(b) by 0 days.

(21) Appl. No.: 14/780,124

(22) PCT Filed: Mar. 27, 2014

(86) PCT No.: PCT/NZ2014/000053
§ 371 (c)(1),
(2) Date: Sep. 25, 2015

(87) PCT Pub. No.: WO2014/158033
PCT Pub. Date: Oct. 2, 2014

(65) Prior Publication Data
US 2016/0030356 A1    Feb. 4, 2016

(30) Foreign Application Priority Data

Mar. 27, 2013 (NZ) .................................. 608784

(51) Int. Cl.
*A61K 9/28* (2006.01)
*A61K 9/20* (2006.01)
*A61K 31/593* (2006.01)

(52) U.S. Cl.
CPC .......... *A61K 9/2068* (2013.01); *A61K 9/2009* (2013.01); *A61K 9/2013* (2013.01); *A61K 9/2018* (2013.01); *A61K 9/2095* (2013.01); *A61K 9/284* (2013.01); *A61K 9/2866* (2013.01); *A61K 9/2893* (2013.01); *A61K 31/593* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 4,929,610 A | 5/1990 | Meier et al. | |
| 5,804,573 A | 9/1998 | Silver | |
| 8,057,819 B2 | 11/2011 | Ross | |
| 2,937,091 A1 | 5/2015 | Rosenberg | |
| 2005/0032741 A1* | 2/2005 | Venkataraman | A61K 31/525 514/52 |

FOREIGN PATENT DOCUMENTS

| | | | |
|---|---|---|---|
| CH | WO 03035027 A1 * | 5/2003 | ........... A61K 9/0056 |
| CN | 101401809 A * | 1/2009 | |
| CN | 101444273 | 6/2009 | |
| CN | 102973528 | 3/2013 | |
| EP | 2201937 | 6/2010 | |
| EP | 2468265 | 6/2012 | |
| SK | 1211699 | 1/2000 | |
| WO | 03/059358 | 7/2003 | |
| WO | 2005/094333 | 10/2005 | |
| WO | 2011/161236 | 12/2011 | |
| WO | 2012/117236 | 2/2012 | |
| WO | 2012/047098 | 4/2012 | |

OTHER PUBLICATIONS http://www.medicines.ie/medicine/14534/SPC/Caltrate+600mg+400IU+Film-coated+ . . . (Dec. 15, 2015).

* cited by examiner

*Primary Examiner* — Susan Tran
(74) *Attorney, Agent, or Firm* — McDonnell Boehnen Hulbert & Berghoff LLP

(57) ABSTRACT

The present invention relates to stable solid formulations of vitamin $D_3$ and to processes for preparation of the same. The present invention provides stabilized compositions comprising vitamin $D_3$ at least one lipophilic dispersant, one or more antioxidants, at least one adsorbent and one or more pharmaceutically acceptable excipients and further coated with a barrier coating.

19 Claims, No Drawings

STABILIZED VITAMIN D FORMULATIONS

CROSS-REFERENCE TO RELATED APPLICATIONS

This application is a US national phase application of International Patent Application No. PCT/NZ2014/000053 filed on 27 Mar. 2014, which claims the benefit of the filing date of New Zealand patent application Serial No. 60874 filed 27 Mar. 2013.

FIELD OF THE INVENTION

The present invention provides stabilized compositions of vitamin D. Particularly the present invention provides compositions comprising vitamin $D_3$ wherein the stability of the said vitamin $D_3$ is improved. The present invention further provides a simple and cost-effective process for the preparation of stabilized compositions of vitamin $D_3$. In one embodiment the present invention also provides a high dose vitamin $D_3$ preparation.

BACKGROUND OF THE INVENTION

Vitamin D is a fat soluble vitamin that is found in food and is also made in the body after exposure to ultraviolet (UV) rays from the sun. Sunshine is a significant source of vitamin D because UV rays from sunlight trigger vitamin D synthesis in the skin. Vitamin D exists in several forms, each with a different level of activity. Vitamin $D_3$ (cholecalciferol) is a non-activated form of vitamin D. It is a precursor of the hydroxylated, biologically active metabolites and analogues of vitamin $D_3$. Generally cholecalciferol is activated by the liver via hydroxylation into 25-hydroxy-cholecalciferol. 25-hydroxy-cholecalciferol is further hydroxylated by the kidney at the 1-alpha-position to 1,25-dihydroxy-cholecalciferol (an active form of vitamin $D_3$).

Vitamin D insufficiency is recognized as a cause of metabolic bone disease in adults that is characterized by the impairment of calcium and phosphate absorption. Vitamin D deficiency is also characterized by impaired bone mineralization. Sustained vitamin D insufficiency and deficiency are considered to be an important cause of gradual bone loss. Vitamin $D_3$ (cholecalciferol) is implicated in numerous disorders. Cholecalciferol has been known to be intimately associated with regulation of calcium levels and bone metabolism and is implicated in osteomalacia, osteoporosis, osteopenia, fibrogenesis imperfecta ossium and rickets. Vitamin $D_3$ increases calcium absorption from the gut and consequently plasma calcium, and suppresses secondary hyperparathyroidism and its skeletal consequences.

Cholecalciferol is known to be highly unstable. The major cause of this instability is its degradation particularly in the presence of oxygen and humidity. This lack of stability may often be detected as a drop in the level of cholecalciferol in a formulation. It has therefore been difficult to develop and market stable formulations of cholecalciferol.

Some attempts have been made to provide compositions of vitamin D3. PCT Publication WO2012/117236 discusses a pharmaceutical composition of at least 20,000 IU of vitamin D3 and a lipid based carrier excipient comprising an oil or mixture of oils in HPMC capsule. U.S. Pat. No. 5,804,573 discusses solid pharmaceutical compositions of active derivatives of vitamin D2 and vitamin D3 comprising at least one pharmaceutically acceptable antioxidant, a polyoxyalkyl stabilizer, and at least one solid pharmaceutical excipient or carrier. EP Patent Application 2201937A1 discloses a multiparticulate pharmaceutical delivery system of vitamin D or derivatives thereof comprising an inert core, an inner layer comprising vitamin D or derivative thereof, an emulsifier and an antioxidant, and an outer protective layer. U.S. Pat. No. 4,929,610 discusses pharmaceutical compositions wherein a pharmaceutical carrier is combined with a mixture of hydroxylated derivatives of vitamin D. In these compositions active substances are dissolved in a pharmaceutically usable solvent such as alcohol, propylene glycol, glycerine or polyethylene glycol and surface active agents are added therein. These mixtures are then filled in hard or soft gelatin capsules. WO03/059358 discloses an oil composition comprising 25-hydroxy vitamin D3 dissolved in the oil in an amount between 5% and 50% by weight of the total weight of the oil composition. This oil composition is then provided in the form of an emulsion, or microencapsulated oil, or a feed premix.

The above attempts, however, either use tedious processes for preparation of the compositions or provide liquid or oily compositions or are unlikely to remain stable over the shelf life of the product. Furthermore liquid or oil based formulations tend to be unstable or go rancid thereby affecting the potency as well as the taste of the product.

The present inventors after intensive research provide stabilized formulations of vitamin D, particularly vitamin D3 that remain stable over prolonged time periods even at accelerated storage conditions. The formulations of the present invention can further be employed to even provide high IU doses of the said vitamin without compromising on its stability and activity. The present inventors provide stable compositions of vitamin D3 without compromising on the desired release of the vitamin. The compositions of the present invention are prepared by simple cost-effective processes that provide the required homogeneity of distribution of vitamin D3 in the dosage form.

It is an object of the present invention to provide stabilized vitamin D formulations, and methods for preparing such formulations, or to at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

The present invention generally relates to stable solid formulations comprising vitamin $D_3$, at least one lipophilic dispersant, one or more antioxidants, at least one adsorbent and one or more pharmaceutically acceptable excipients. Particularly the present invention relates to stable solid tablet formulation of vitamin $D_3$ comprising a tablet core comprising vitamin $D_3$, at least one lipophilic dispersant, one or more antioxidants, at least one adsorbent and one or more pharmaceutically acceptable excipients; and at least one barrier coating.

In a first aspect the invention relates to a stable solid tablet formulation of vitamin D3 comprising:
 (a) a tablet core comprising vitamin $D_3$, at least one lipophilic dispersant, one or more antioxidants, at least one adsorbent and one or more pharmaceutically acceptable excipients; and
 (b) at least one barrier coating.

In one embodiment the vitamin D3 is substantially uniformly dispersed throughout the tablet core.

In one embodiment the lipophilic dispersant is a wax, a fatty acid, a long chain monohydric alcohol, a fat or combinations thereof. In a preferred embodiment the fatty acid is a hydrogenated vegetable oil. In a particularly contemplated embodiment the hydrogenated vegetable oil is hydrogenated castor oil, hydrogenated palm oil, hydrogenated peanut oil, hydrogenated rapeseed oil, hydrogenated rice bran oil, hydrogenated soybean oil, hydrogenated cottonseed oil, hydrogenated sunflower oil, or mixtures thereof.

In one embodiment the antioxidant is tocopherol, tocopherol acetate, tocopherol acid succinate, β-carotene, propyl gallate, butylated hydroxytoluene (BHT), butylated hydroxyanisole, vitamin E, ascorbic acid, sodium ascorbate, calcium ascorbate, ascorbic palmitate, 2,4,5-trihydroxybutyrophenone, 4-hydroxymethyl-2,6-di-tert-butylphenol, erythorbic acid, gum guaiac, thiodipropionic acid, dilauryl thiodipropionate, tertbutylhydroquinone or combinations thereof.

In one embodiment the adsorbent is mannitol, dibasic calcium phosphate, dicalcium phosphate dihydrate, calcium hydrogen phosphate dihydrate, calcium phosphate tribasic, or combinations thereof. In a preferred embodiment the adsorbent is dibasic calcium phosphate, dicalcium phosphate dihydrate, or calcium hydrogen phosphate dihydrate. In a particularly contemplated embodiment the adsorbent is mannitol.

In one embodiment the pharmaceutically acceptable excipient is a diluent, binder, disintegrant, lubricant, colorant, coating agent, anti-adherent, glidant, or combinations thereof.

In one embodiment the barrier coating comprises hydroxypropyl methylcellulose, polyvinyl alcohol, polyvinyl acetate, sodium carboxymethyl cellulose, pullulan, polyvinyl alcohol and vinyl alcohol-ethylene glycol copolymer; copolymer comprising methyl methacrylate and diethylaminoethyl methacrylate, poylmethacrylic acids, polymethacrylates or combinations thereof. In a particularly contemplated embodiment the barrier coating comprises polyvinyl alcohol.

In one embodiment the formulation comprises:
(a) a tablet core comprising vitamin $D_3$, hydrogenated vegetable oil, butylated hydroxyanisole, mannitol, and magnesium stearate; and
(b) a barrier coating.

In another embodiment the formulation comprises:
(a) a tablet core comprising vitamin $D_3$, hydrogenated castor oil, butylated hydroxyanisole, butylated hydroxytoluene, dicalcium phosphate dihydrate, croscarmellose sodium, and magnesium stearate; and
(b) a barrier coating.

In a further embodiment the formulation comprises:
(a) a tablet core comprising vitamin $D_3$, hydrogenated castor oil, butylated hydroxyanisole, butylated hydroxytoluene, dicalcium phosphate dihydrate, croscarmellose sodium, colloidal anhydrous silica, and magnesium stearate; and
(b) a barrier coating.

In one embodiment the formulation is in the form of a monolithic tablet dosage form.

In one embodiment the formulation comprises about 100 IU to about 75,000 IU of vitamin D3, about 1,000 IU to about 65,000 IU of vitamin D3, or about 40,000 IU to about 65,000 IU of vitamin D3. In one embodiment the formulation comprises about 7,000 IU of vitamin D3. In another embodiment the formulation comprises about 50,000 IU of vitamin D3.

In one embodiment the formulation comprises vitamin D3 in an amount of about 0.01% to about 25%, about 0.1% to about 20%, or about 0.3% to about 20% by weight of the composition.

In one embodiment the ratio of lipophilic dispersant to the vitamin D3 is not more than about 85.

In one embodiment the formulation comprises less than about 2% by weight of total impurities after 6 months at 40° C. and 75% relative humidity.

In one embodiment the vitamin D3 in the formulation is stable for at least about six months at 25° C. and 60% relative humidity as determined by HPLC analysis.

In one embodiment the formulation retains after at least about six months at 25° C. and 60% relative humidity at least 90%, at least 95% or at least 98% of the vitamin D3 initially present in the formulation as determined by HPLC analysis.

In one embodiment the tablet core comprises
i. granules comprising vitamin $D_3$, at least one lipophilic dispersant, one or more antioxidants and optionally one or more pharmaceutically acceptable excipients;
ii. at least one adsorbent; and
iii. one or more pharmaceutically acceptable excipients.

In another embodiment the tablet core comprises
i. granules comprising vitamin $D_3$, at least one lipophilic dispersant, one or more antioxidants, at least one adsorbent and optionally one or more pharmaceutically acceptable excipients;
ii. at least one adsorbent; and
iii. one or more pharmaceutically acceptable excipients.

In a second aspect the invention relates to a process of preparing the formulation of the invention comprising the steps of:
(a) dissolving at least one antioxidant in a suitable solvent,
(b) dissolving vitamin $D_3$ in the solution of step (a),
(c) melting the lipophilic dispersant,
(d) adding the solution of step (b) into the melted dispersant of step (c),
(e) incorporating a partial or complete amount of at least one adsorbent in the melted mass of step (d) followed by cooling the mixture,
(f) sizing the cooled mass of step (e) and sifting to obtain granules,
(g) blending the granules of step (f) with the remaining pharmaceutically acceptable excipients and partial amount of the adsorbent, if any, followed by lubricating the blend,
(h) compressing the lubricated blend of step (g) into tablets, and
(i) coating the compressed tablets of step (h) with at least one barrier coating.

In one embodiment the process of preparing the formulation comprises the steps of:
(a) blending a vitamin $D_3$ blend containing a lipophilic dispersant and an antioxidant with at least one adsorbent,
(b) lubricating the blend of step (a),
(c) compressing the lubricated blend of step (b) into tablets; and
(d) coating the compressed tablets of step (c) with at least one barrier coating.

In a third aspect the invention relates to a method of treating or preventing conditions associated with vitamin $D_3$ insufficiency or deficiency by administering to a subject in need thereof the formulation of the invention.

In a fourth aspect the invention relates to the formulation of the invention for use in treating or preventing conditions associated with vitamin D3 insufficiency or deficiency.

In a fifth aspect the invention relates to the use of the formulation of the invention in the manufacture of a medicament for treating or preventing conditions associated with vitamin D3 insufficiency or deficiency.

In one embodiment the condition associated with vitamin D3 insufficiency or deficiency is osteomalacia, osteoporosis, osteopenia, fibrogenesis imperfecta ossium, rickets or hypocalcaemia. In a particularly contemplated embodiment the condition associated with vitamin D3 insufficiency or deficiency is osteoporosis.

DETAILED DESCRIPTION OF THE INVENTION

The compositions of the present invention comprise vitamin D, at least one lipophilic dispersant, one or more antioxidants, at least one stabilizing adsorbent and one or more pharmaceutically acceptable excipients. In one embodiment, the present invention relates to compositions comprising vitamin D3, at least one lipophilic dispersant, one or more antioxidants, at least one stabilizing adsorbent and one or more pharmaceutically acceptable excipients.

In one embodiment, the compositions of the present invention comprising vitamin D, at least one lipophilic dispersant, one or more antioxidants, at least one stabilizing adsorbent, and one or more pharmaceutically acceptable excipients is further coated with at least one barrier coating. In another embodiment, the compositions of the present invention comprising vitamin D3, at least one lipophilic dispersant, one or more antioxidants, at least one stabilizing adsorbent, and one or more pharmaceutically acceptable excipients is further coated with at least one barrier coating.

Vitamin D that may be employed in the compositions of the present invention includes, but is not limited to, vitamin D2, vitamin D3 or cholecalciferol and the like or isomers, derivatives or combinations thereof. Vitamin D that may be employed in the compositions of the present invention may be a solid or an oily liquid. Vitamin D that may be employed in the compositions of the present invention may be of crystalline or amorphous form. In one embodiment, the vitamin D employed is vitamin D3 or cholecalciferol. In another embodiment, vitamin D employed in the compositions of the present invention is vitamin D3 or choleclaciferol or derivatives thereof such as but not limited to, 1α-hydroxycholecalciferol, 25-hydroxycholecalciferol, 1α,25-hydroxycholecalciferol, 24,25-hydroxycholecalciferol, and the like or combinations thereof. Vitamin D3 that may be employed in the compositions of the present invention may be a solid or an oily liquid. Vitamin D3 that may be employed in the compositions of the present invention may be of crystalline or amorphous form. In another embodiment, vitamin D3 employed in the composition of the present invention is in the form of a crystalline solid.

Cholecaliferol or vitamin D3 may be used in the compositions of the present invention in a range of about 100 IU to about 75,000 IU per unit dosage form. In another embodiment, vitamin D3 is used in the compositions of the present invention in the range of about 400 IU to about 70,000 IU. In a further embodiment, vitamin D3 is used in the compositions of the present invention in the range of about 10,000 IU to about 65,000 IU. In another embodiment, vitamin D3 is used in the compositions of the present invention in the range of about 10,000 IU to about 60,000 IU. In one embodiment, vitamin D3 is used in the compositions of the present invention in the range of about 20,000 IU to about 60,000 IU. In a further embodiment, vitamin D3 is used in the compositions of the present invention in the range of about 40,000 IU to about 65,000 IU. In still another embodiment, vitamin D3 is used in the compositions of the present invention in the range of about 20,000 IU to about 55,000 IU. In a further embodiment, vitamin D3 used in the compositions of the present invention is about 50,000 IU. Further, the compositions of the present invention may comprise about 0.01% to about 25% by weight of the composition of vitamin D3. In another embodiment, the compositions of the present invention may comprise about 0.1% to about 20% by weight of the composition of vitamin D3. In a further embodiment, the compositions of the present invention may comprise about 0.3% to about 15% by weight of the composition of vitamin D3. In yet another embodiment, the compositions of the present invention may comprise about 0.5% to about 10% by weight of the composition of vitamin D3. In one embodiment, the compositions of the present invention comprise less than about 2% by weight of the composition of vitamin D3. In another embodiment, the compositions of the present invention comprise less than about 1% by weight of the composition of vitamin D3. In a further embodiment, appropriate amount of overages may be added in the compositions of the present invention to account for process loss or degradation, if any. In one embodiment, crystalline vitamin D3 is employed in the compositions of the present invention. In another embodiment, vitamin D3 employed in the present invention may be obtained commercially as granules, powder and the like or mixtures thereof. In one embodiment, vitamin D3 commercially available as a blend with lipophilic dispersant and antioxidant may be employed in the present invention. In another embodiment, vitamin D3 commercially available as a powder consisting of vitamin D3, lipophilic dispersant, and antioxidant may be employed in the present invention.

The compositions of the present invention further comprise at least one lipophilic dispersant. Without being bound by any theory it is believed that the lipophilic dispersant that is used in the compositions of the present invention is a lipophilic carrier which aids in the uniform distribution of vitamin D in the formulation. In one embodiment the lipophilic dispersant employed in the formulation of the present invention in addition to aiding the uniform dispersion of vitamin D in the formulation also aids in improving the stability of the vitamin. It is further believed that the lipophilic dispersant protects the vitamin by preventing any moisture ingress and degradation of the vitamin during the shelf life of the product.

In a further embodiment, one or more lipophilic dispersants that may be included in the composition of the present invention include, but are not limited to, waxes, fatty acids, long chain monohydric alcohols, fats, and the like or combinations thereof. A fatty acid is a carboxylic acid with a long aliphatic chain, which is either saturated or unsaturated. Most naturally occurring fatty acids have a chain of carbon atoms from 4 to 28. Fatty acids that may be employed in the compositions of the present invention are hydrogenated vegetable oils. Suitable hydrogenated vegetable oils may be selected from, but not limited to, hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil, hydrogenated castor oil, and the like, and mixtures thereof. Other fatty acids that may be employed include, but are not limited to, decenoic acid, docosanoic acid, stearic acid, palmitic acid, lauric acid, myristic acid, and the like, and mixtures thereof. Long chain monohydric alcohols that may be employed include, but are not limited to, cetyl alcohol, stearyl alcohol and the like or mixtures thereof. Waxes typically are esters of fatty acids with long chain monohydric alcohols. Natural waxes are often mixtures of such esters, and may also contain hydrocarbons. Synthetic waxes are long-chain hydrocarbons. Waxes that may be employed in the compositions of the present invention include natural waxes, such as animal waxes, vegetable waxes, and petroleum waxes (i.e., paraffin waxes, microcrystalline waxes, petrolatum waxes, mineral waxes), and synthetic waxes. Suitable examples include, but are not limited to, spermaceti wax, carnauba wax, Japan wax, bayberry wax, flax wax, beeswax, Chinese wax, shellac wax, lanolin wax, sugarcane wax, candelilla wax, paraffin wax, microcrystalline wax, petrolatum wax, carbowax, and the like, and mixtures thereof. Mixtures of these waxes with the fatty acids set out above may also be used. The wax may also be a mono-, di- or tri-glyceryl ester (glycerides) which is an ester formed from a fatty acid having from about 10 to about 22 carbon atoms and glycerol, wherein one or more of the hydroxyl groups of glycerol is substituted by a fatty acid. Examples of useful glycerides include glyceryl monostearate, glyceryl distearate, glyceryl tristearate, glyceryl dipalmitate, glyceryl tripalmitate, glyceryl monopalmitate, glyceryl dilaurate, glyceryl trilaurate, glyceryl monolaurate, glyceryl didocosanoate, glyceryl tridocosanoate, glyceryl monodocosanoate, glyceryl monocaproate, glyceryl dicaproate, glyceryl tricaproate, glyceryl monomyristate, glyceryl dimyristate, glyceryl palmitostearate, glyceryl trimyristate, glyceryl monodecenoate, glyceryl didecenoate, polyglyceryl diisostearate, glyceryl tridecenoate, glyceryl behenate, lauroyl macrogolglycerides and the like, and mixtures thereof. In one embodiment, the lipophilic dispersant that may be employed is in the form of, but not limited to, a semisolid, a waxy or a solid substance. In a further embodiment, the lipophilic dispersant employed in the compositions of the present invention is a hydrogenated vegetable oil.

In one embodiment, the compositions of the present invention comprise at least one lipophilic dispersant in an amount of about 0.1% to about 80% by weight of the dosage form. In a further embodiment, the compositions of the present invention comprise at least one lipophilic dispersant in an amount of about 0.5% to about 75% by weight of the dosage form. In another embodiment, the compositions of the present invention comprise at least one lipophilic dispersant in an amount of about 1% to about 70% by weight of the dosage form. In another embodiment, the ratio of lipophilic dispersant to the vitamin D3 is more than about 1. In another embodiment, the ratio of lipophilic dispersant to the vitamin is not more than 75. In another embodiment, the ratio of lipophilic dispersant to the vitamin D3 is not more than about 85. In one embodiment, the ratio of lipophilic dispersant to vitamin D3 can be adjusted such that release of vitamin D3 from the formulations of the present invention is as desired.

The compositions of the present invention further comprise at least one antioxidant. Suitable antioxidants that may be employed in the compositions of the present invention include, but are not limited to, tocopherol, tocopherol acetate, tocopherol acid succinate, β-carotene, propyl gallate, butylated hydroxytoluene (BHT), butylated hydroxyanisole (BHA), vitamin E, ascorbic acid, sodium ascorbate, calcium ascorbate, ascorbic palmitate, 2,4,5-trihydroxybutyrophenone, 4-hydroxymethyl-2,6-di-tert-butylphenol, erythorbic acid, gum guaiac, thiodipropionic acid, dilauryl thiodipropionate, tertbutylhydroquinone and the like or combinations thereof, including pharmaceutically acceptable salts and esters thereof. In one embodiment, the compositions of the present invention may comprise at least one antioxidant in an amount of about 0.01% to about 20% by weight of the composition.

In one embodiment the compositions of the present invention in addition to vitamin D3, at least one lipophilic dispersant and at least one antioxidant further comprise one or more stabilizing adsorbents or adsorbents. Suitable stabilizing adsorbents that may be employed in the compositions of the present invention include, but are not limited to, polyols, microcrystalline cellulose, starch, corn starch, modified starch, lactose, calcium phosphate-dibasic, dicalcium phosphate dihydrate, calcium hydrogen phosphate dihydrate, calcium phosphate-tribasic, calcium sulfate, and the like or combinations thereof. Suitable polyols that may be employed include, but are not limited to, mannitol, lactitol, maltitol, erythritol and the like or combinations thereof. In a further embodiment, the stabilizing adsorbent employed in the compositions of the present invention is mannitol, calcium phosphate dibasic, dicalcium phosphate dihydrate, calcium hydrogen phosphate dihydrate, or combinations thereof. In one embodiment, the adsorbent employed is mannitol. In another embodiment, the adsorbent employed is dibasic calcium phosphate, dicalcium phosphate dihydrate, or calcium hydrogen phosphate dihydrate. In one embodiment, the compositions of the present invention may comprise at least one stabilizing adsorbent in an amount of about 5% to about 95% by weight of the composition. In one embodiment, the ratio of lipophilic dispersant to adsorbent employed in the composition of the present invention is about 0.001 to about 10. In a further embodiment, the ratio of lipophilic dispersant to adsorbent employed in the compositions of the present invention is about 0.005 to about 7. In yet another embodiment, the ratio of lipophilic dispersant to adsorbent employed in the composition of the present invention is about 0.01 to about 5.

Without being bound to any theory it is believed that the adsorbent may either due to its hydrophobic nature reduce contact with any moisture or reduce degradation of vitamin D3 or may due to its preferential water binding property reduce impact of moisture on the vitamin.

The stabilized pharmaceutical compositions of the present invention further comprise one or more pharmaceutically acceptable excipients such as, but are not limited to, diluents, binders, disintegrants, lubricants, colorants, coating agents, anti-adherents, gildants, and the like.

The present invention may include one or more diluents such as, but not limited to, microcrystalline cellulose, corn starch, pregelatinized starch, lactose, lactose monohydrate, sugar, dextrate, dextrate hydrated, dextrins, fructose, modified corn starch, inorganic salts such as calcium carbonate, calcium phosphate-dibasic, calcium phosphate-tribasic, calcium sulfate and/or cellulose derivatives, and the like or mixtures. The binders that may be employed in the dosage form include, but are not limited to, copovidone, starch, microcrystalline cellulose, highly dispersed silica, lactose, polyethylene glycol, polyvinylpyrrolidone, vinyl copolymers, povidone, polymethacrylic acid derivative, ethyl cellulose, cross-linked carboxymethylcellulose, hydroxypropyl methyl cellulose, hydroxypropylcellulose, natural or synthetic gums and the like or mixtures thereof. The lubricants that may be employed in the dosage form include, but are not limited to, magnesium stearate, stearic acid, palmitic acid, calcium stearate, talc, polyethylene glycol, colloidal silicon dioxide, sodium stearyl fumarate, and the like and mixtures thereof. Compositions of the present invention may optionally also include a glidant such as, but not limited to, colloidal silica, silica gel, precipitated silica, or combinations thereof. Anti-adherents may be employed in the dosage form such as, but are not limited to, talc, magnesium stearate or finely divided silica, and the like or combinations thereof. Disintegrants that may be employed include, but are not limited to crospovidone, sodium starch glycolate, natural or modified pregelatinized starch, croscarmellose sodium, low-substituted hydroxypropyl cellulose, calcium silicate and the like or combinations thereof.

In a further embodiment, the stabilized formulations of the present invention may be in the form of a solid dosage form. In one embodiment, the stabilized formulations of the present invention may be in the form of tablets, capsules, granules, and the like. In a further embodiment, the solid dosage form of the present invention is in the form of a tablet. The term "composition" or "formulation" or "dosage form" has been employed interchangeably for the purpose of the present invention and mean that it is a pharmaceutical composition which is suitable for administration to a patient.

In a further embodiment, the solid dosage form of the present invention is coated with at least one barrier coating. Without being bound to any theory it is believed that the barrier coating is an oxygen and/or moisture barrier and helps maintain the stability of the formulation during storage. Suitable barrier coatings that may be employed include but are not limited to, hydroxypropyl methylcellulose, polyvinyl alcohol, polyvinyl acetate, sodium carboxymethyl cellulose, pullulan, polyvinyl alcohol and vinyl alcohol-ethylene glycol copolymer; copolymer comprising methyl methacrylate and diethylaminoethyl methacrylate; poylmethacrylic acids, polymethacrylates, and the like or combinations thereof. In one embodiment, the barrier coating employed is polyvinyl alcohol. In a further embodiment the coating agents employed in the compositions of the present invention are commercially available under the trade names such as, but not limited to, Opadry® II, Opadry® Fx™, Opadry® AMB, Opadry® 21K58794 White, Opadry® FX 63F97546 Silver, Kollicoat® Protect, Kollicoat® Smartseal 30D, Aquarius® MG, INSTAMOISTSHIELD AQUA II, and the like or combinations thereof. In a further embodiment, the barrier coating employed in the compositions of the present invention is Opadry® FX 63F97546. In another embodiment, the barrier coating employed in the compositions of the present invention is Opadry® II 85F18422 White. In a further embodiment, the barrier coating of Opadry® II 85F18422 White and Opadry® FX 63F97546 is employed. In another embodiment, the barrier coating of Opadry® II 85F18422 White is applied followed by a further coating of Opadry® FX 63F97546. Opadry® II 85F18422 White and Opadry® FX 63F97546 employed in one embodiment of the present invention as a barrier coating agent, comprises polyvinyl alcohol. In another embodiment, the barrier coating employed in the compositions of the present invention comprises polyvinyl alcohol.

Further without being bound by theory it is believed that the lipophilic dispersant, antioxidant, adsorbent and barrier coating work synergistically to provide stable formulations of vitamin D3 of the present invention.

In another embodiment, the solid pharmaceutical compositions of the present invention may be in the form of matrix dosage form. In yet another embodiment, the solid pharmaceutical compositions of the present invention may be in the form of a monolithic tablet. In a further embodiment, the solid pharmaceutical compositions of the present invention may be in the form of a multilayered tablet. In one embodiment, the solid pharmaceutical compositions of the present invention may be in the form of a bi-layered tablet. In one embodiment, the composition of the present invention is a stable solid monolithic dosage form.

In one embodiment, the solid dosage form of the present invention is in the form of tablet comprising a tablet core and at least one barrier coating. In one embodiment, one or more coats of same or different barrier coatings are applied to the tablet cores. In a further embodiment, the stable solid tablet formulation of vitamin D3 of the present invention comprises: (a) tablet core comprising vitamin D3, at least one lipophilic dispersant, one or more antioxidants, at least one adsorbent and one or more pharmaceutically acceptable excipients; and (b) at least one barrier coating.

In one embodiment, the compositions of the present invention comprise (a) granules comprising (i) vitamin D3, (ii) at least one lipophilic dispersant, (iii) one or more antioxidants, and (iv) at least one stabilizing adsorbent; and (b) one or more pharmaceutically acceptable excipients. In another embodiment, the compositions of the present invention, comprise (a) granules comprising (i) vitamin D3, (ii) at least one lipophilic dispersant, and (iii) one or more antioxidants, (b) at least one stabilizing adsorbent; and (c) one or more pharmaceutically acceptable excipients. In a further embodiment, the compositions of the present invention comprise (a) granules comprising (i) vitamin D3, (ii) at least one lipophilic dispersant, (iii) one or more antioxidants, (iv) at least one stabilizing adsorbent and (v) one or more pharmaceutically acceptable excipients; and (b) one or more pharmaceutically acceptable excipients. In another embodiment, the compositions of the present invention, comprise (a) granules comprising (i) vitamin D3, (ii) at least one lipophilic dispersant, (iii) one or more antioxidants and (iv) one or more pharmaceutically acceptable excipients, (b) at least one stabilizing adsorbent; and (c) one or more pharmaceutically acceptable excipients. In a further embodiment, the compositions of the present invention comprise (a) granules comprising (i) vitamin D3, (ii) at least one lipophilic dispersant, (iii) one or more antioxidants, (iv) at least one stabilizing adsorbent and (v) one or more pharmaceutically acceptable excipients; (b) at least one stabilizing adsorbent and (c) one or more pharmaceutically acceptable excipients.

In one embodiment, the dosage form of vitamin D3 of the present invention comprises (a) tablet core comprising vitamin D3, at least one lipophilic dispersant, one or more antioxidants, at least one adsorbent and one or more pharmaceutically acceptable excipients; and (b) at least one barrier coating. In another embodiment, the dosage form of vitamin D3 of the present invention comprises: (a) tablet core comprising: i. granules of vitamin D3, at least one lipophilic dispersant, one or more antioxidants and optionally one or more pharmaceutically acceptable excipient; ii. at least one adsorbent; and iii. one or more pharmaceutically acceptable excipients; and (b) at least one barrier coating. In a further embodiment, the dosage form of vitamin D3 of the present invention comprises: (a) tablet core comprising: i. granules of vitamin D3, at least one lipophilic dispersant, one or more antioxidants, at least one adsorbent and optionally one or more pharmaceutically acceptable excipient; ii. at least one adsorbent; and iii. one or more pharmaceutically acceptable excipients; and (b) at least one barrier coating.

In one embodiment, the composition of the present invention comprises (a) tablet core comprising at least one lipophilic dispersant, one or more antioxidants, at least one adsorbent and one or more pharmaceutically acceptable excipients; and (b) at least one barrier coating comprising polyvinyl alcohol. In a further embodiment, the composition of the present invention comprises (a) tablet core comprising vitamin D3, hydrogenated vegetable oil, butylated hydroxytoluene, butylated hydroxyanisole, calcium hydrogen phosphate dihydrate and one or more pharmaceutically acceptable excipients; and (b) at least one barrier coating comprising polyvinyl alcohol.

In one embodiment the vitamin D3 is substantially uniformly dispersed throughout the tablet core.

The compositions of the present invention can be prepared by processes such as, but not limited to, wet granulation, dry granulation, melt granulation, direct compression, melt extrusion, spray coating, fluidized bed coating, spray congealing and the like. In one embodiment, the vitamin D3 is dispersed uniformly in a solvent along with the antioxidant, which is then added to a lipophilic dispersant to achieve the desired content uniformity. Suitable solvents that may be employed include but are not limited to, aqueous, organic, hydroalcoholic solvents. Examples of suitable solvents include isopropyl alcohol, ethanol, water and the like.

In one embodiment, the process of preparing the composition of the present invention comprises the steps of:
(a) dissolving at least one antioxidant in suitable solvent
(b) dissolving vitamin $D_3$ in the solution of step (a)
(c) melting the lipophilic dispersant or carrier
(d) adding the solution of step (b) into the melted dispersant or carrier of step (c)
(e) incorporating part or complete amount of at least one stabilizing adsorbent in the melted mass of step (d) followed by cooling the mixture
(f) sizing the cooled mass of step (e) and sifting to obtain granules
(g) blending the granules of step (f) with the remaining pharmaceutically acceptable excipients and part of stabilizing adsorbent if any, followed by lubricating the blend
(h) compressing the lubricated blend of step (g) into tablets; and
(i) coating the compressed tablets of step (h) with at least one barrier coating In another embodiment, the process of preparing the composition of the present invention comprises the steps of:
(a) blending vitamin $D_3$ blend containing lipophilic dispersant and antioxidant with stabilizing adsorbent
(b) lubricating the blend of step (a)
(c) compressing the lubricated blend of step (b) into tablets; and
(d) coating the compressed tablets of step (c) with at least one barrier coating.

The stability of the composition of the present invention was investigated under various storage conditions of 25° C./60% RH, 30° C./65% RH, and 40° C./75RH. It was observed that even after a period of 6 months at the above temperature and relative humidity conditions, the composition of the present invention was stable and no significant reduction in the level of vitamin D3 was observed. In one embodiment, the amount of vitamin D3 in the formulation or assay thereof is determined by HPLC method of analysis. In one embodiment, formulations of the present invention stored under the above conditions retain at least 80% of the vitamin D3 present in the composition at the time of storage. In another embodiment, formulations of the present invention stored under the above conditions retain at least 85% of the vitamin D3 present in the composition at the time of storage. In a further embodiment, formulations of the present invention stored under the above conditions retain at least 90% of the vitamin D3 present in the composition at the time of storage. In a further embodiment, formulations of the present invention stored under the above conditions retain at least 95% of the vitamin D3 present in the composition at the time of storage. In a further embodiment, formulations of the present invention stored under the above conditions retain 100% of the vitamin D3 present in the composition at the time of storage. In one embodiment, the vitamin D3 in the formulation is stable for at least about six months at 25° C. and 60% relative humidity as determined by HPLC analysis. For example, in one embodiment the formulation retains after at least about six months at 25° C. and 60% relative humidity at least 90% of the vitamin D3 initially present in the formulation as determined by HPLC analysis. In another embodiment the formulation retains after at least about six months at 25° C. and 60% relative humidity at least 95% of the vitamin D3 initially present in the formulation as determined by HPLC analysis. In a further embodiment the formulation retains after at least about six months at 25° C. and 60% relative humidity at least 98% of the vitamin D3 initially present in the formulation as determined by HPLC analysis. In still a further embodiment the formulation retains after at least about six months at 25° C. and 60% relative humidity at least 99% of the vitamin D3 initially present in the formulation as determined by HPLC analysis.

In another embodiment, the compositions of the present invention have less than 2% by weight of total impurities after 6 months at 40° C./75% RH. In a further embodiment, the total impurities determined in the compositions include impurity A (trans-cholecalciferol) and unspecified impurities.

In one embodiment, the compositions of the present invention also provide desired in-vitro release profile. In a further, embodiment, the solid dosage forms of the present invention disintegrate within 30 minutes. In yet another embodiment, the solid dosage forms of the present invention disintegrate within 15 minutes. In another embodiment, the solid dosage forms of the present invention disintegrate within 10 minutes. Without being bound to any theory, it is believed that quicker disintegration of the tablets provides vitamin D3 earlier for absorption and action.

The present invention further relates to the use of the stabilized compositions of the present invention for the prevention or treatment of conditions associated with vitamin D insufficiency or deficiency. In a further embodiment the present invention also relates to the use of the stabilized compositions of the present invention for the prevention and treatment of any condition wherein vitamin D serves as a beneficial agent. The present invention also provides a method of treating or preventing conditions associated with vitamin D insufficiency or deficiency by administering to the subject in need thereof stabilized formulations of the present invention. In a further embodiment, the present invention also provides a method of treating or preventing conditions wherein vitamin D serves as a beneficial agent by administering to the subject in need thereof stabilized formulations of the present invention.

The invention further relates to the use of the stabilized formulations of the invention in the manufacture of a medicament for the prevention or treatment of conditions associated with vitamin D insufficiency or deficiency. In a further embodiment, the invention relates to the use of the stabilized formulations of the invention in the manufacture of a medicament for treating or preventing conditions wherein vitamin D serves as a beneficial agent.

In various embodiments the condition associated with vitamin D insufficiency or deficiency is osteomalacia, osteoporosis, osteopenia, fibrogenesis imperfecta ossium, rickets or hypocalcaemia.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The term "comprising" as used in this specification and claims means "consisting at least in part of". When interpreting statements in this specification and claims, which include the term "comprising", other features besides the features prefaced by this term in each statement, can also be present. Related terms such as "comprise" and "comprised" are to be interpreted in similar manner.

While the present invention has been described in terms of its specific embodiments, certain modifications and equivalents will be apparent to those skilled in the art and are intended to be included within the scope of the present invention. Details of the present invention, including its objects and advantages, are provided in the non-limiting exemplary illustrations below.

EXAMPLES

Example 1: Formulation of Vitamin $D_3$ (50,000 IU)

A stabilized formulation of crystalline vitamin D3 was prepared as per the following composition.

TABLE 1

| Composition of vitamin $D_3$ formulation | |
| --- | --- |
| Ingredients | mg/tablet |
| Intra-granular | |
| Crystalline vitamin $D_3$* | 1.69 |
| Butylated hydroxyanisole | 0.5 |
| Isopropyl alcohol | 7 |
| Hydrogenated vegetable oil (Hydrogenated Cottonseed Oil) | 14 |
| Mannitol | 25.3 |
| Extra-granular | |
| Mannitol | 156.51 |
| Magnesium stearate | 2 |

TABLE 1-continued

| Composition of vitamin $D_3$ formulation | |
| --- | --- |
| Ingredients | mg/tablet |
| Coating | |
| Opadry 21K58794 White | 6 |
| Opadry FX 63F97546 Silver | 4.12 |
| Total | 210.120 |

*50,000 IU + overages

Procedure

Butylated hydroxyanisole solution was prepared in isopropyl alcohol. Crystalline vitamin $D_3$ was dissolved in butylated hydroxyanisole solution. Hydrogenated vegetable oil was melted and mixed with the vitamin $D_3$ solution and stirred till all the traces of isopropyl alcohol were evaporated. Intra-granular mannitol was added to the above mixture and cooled up to room temperature. This mass was then sized, sifted and dried to obtain granules. These granules were then blended with extra—granular mannitol and lubricated using magnesium stearate and finally compressed. The compressed tablets were then coated with Opadry 21K58794 White and Opadry FX 63F97546 Silver to form a stabilized tablet formulation of vitamin D3. The formulated tablets had a desirable disintegration time of less than 10 minutes.

Chemical Stability

The chemical stability of this formulation in amber colored glass vials was evaluated for 6 months at 25° C./60% RH and 40° C./75% RH.

The assay for vitamin $D_3$ was done by HPLC method. For the assay, the sample solution was prepared by crushing 5 tablets into fine powder in mortar pestle after determining their average weight. Powder equivalent to 2.5 mg vitamin $D_3$ was weighed into a 100 mL volumetric flask and approximately 35 mL methanol was added therein, followed by sonication for 40 minutes in ice cold water. This solution was further diluted to volume with methanol, mixed well and filtered through a 0.45 µm membrane filter. The sample solution was analyzed using an Agilent Zorbax SB $C_{18}$ (250 mm×4.6 mm, 5 µm) column, maintained at ambient temperature using a 840 ml mobile phase of acetonitrile+140 mL methanol+20 mL water at a flow rate of 1.0 mL/minute under the isocratic elution mode. Detection was made using UV at 265 nm.

Table 2 beneath indicates that the assay, single maximum unspecified impurity and total impurities were within limits during the study. Total impurities include impurity A (trans-cholecalciferol) and total unspecified impurities (inclusive of single maximum unspecified impurity). These impurities are degradants or isomers of vitamin $D_3$. Assay values were found to be in trend with the initial assay values, indicating that the formulation was stable.

TABLE 2

| Assessment of chemical stability | | | | | |
| --- | --- | --- | --- | --- | --- |
| Condition | Assay (%) (only vitamin $D_3$) | Combined Assay (%) (vitamin $D_3$ + precholecalciferol) | Impurity A (%) | Single maximum unspecified impurity (%) | Total impurity (%) |
| Initial | 120.6 | 124.4 | — | 0.06 | 0.10 |
| 1M 40° C./75% RH | 115.3 | 120.1 | — | 0.09 | 0.21 |
| 6M 40° C./75% RH | 96.4 | 100.7 | 0.02 | 0.39 | 1.32 |
| 1M 25° C./60% RH | 118.6 | 124.0 | — | 0.09 | 0.12 |
| 6M 25° C./60% RH | 116.3 | 120.9 | 0.01 | 0.09 | 0.27 |

TABLE 2-continued

Assessment of chemical stability

| Condition | Assay (%) (only vitamin $D_3$) | Combined Assay (%) (vitamin $D_3$ + precholecalciferol) | Impurity A (%) | Single maximum unspecified impurity (%) | Total impurity (%) |
|---|---|---|---|---|---|
| Limits | 90-125% | 90-125% | NMT 0.2% | NMT 1.0% | NMT 2.0% |

Impurity A: trans-cholecalciferol

Example 2: Formulation of Vitamin $D_3$ (50,000 IU)

A stabilized formulation of vitamin $D_3$ was prepared as per the following composition.

TABLE 3

Composition of vitamin $D_3$ formulation

| Ingredients | mg/tablet |
|---|---|
| Vitamin $D_3$ | 1.688 |
| Hydrogenated castor oil | 133.001 |

TABLE 3-continued

Composition of vitamin $D_3$ formulation

| Ingredients | mg/tablet |
|---|---|
| Butylated hydroxyanisole | 0.135 |
| Butylated hydroxytoluene | 0.135 |
| Dicalcium Phosphate Dihydrate | 44 |
| Croscarmellose Sodium | 20 |
| Magnesium Stearate | 1 |
| Coating | |
| Opadry II 85F18422 White | 6.000 |
| Opadry FX 63F97546 Silver | 4.120 |
| Purified water | NA |
| Total | 210.079 |

*50,000 IU + overages

Procedure

Blend of vitamin $D_3$, hydrogenated castor oil, butylated hydroxyanisole and butylated hydroxytoluene was further blended with dicalcium phosphate dihydrate and croscarmellose sodium, lubricated using magnesium stearate and finally compressed. The compressed tablets were then coated with Opadry II 85F18422 white and Opadry FX 63F97546 Silver to form a stabilized tablet formulation of vitamin $D_3$. The formulated tablets had a desirable disintegration time of less than 10 minutes.

Chemical Stability

The chemical stability of this formulation in amber colored glass vials was evaluated for 6 months at 25° C./60% RH and 40° C./75% RH. Table 4 beneath indicates that the assay, single maximum unspecified impurity and total impurities were within limits during the study. Assay values (as determined by the procedure mentioned above) were found to be in trend with initial assay values, indicating that the formulation was stable

TABLE 4

Assessment of chemical stability

| Condition | Assay* (%) (only Vitamin $D_3$) | Combined Assay* (%) (Vitamin $D_3$ + Precholecalciferol) | Impurity A (%) | Single maximum unspecified impurity (%) | Total impurity (%) |
|---|---|---|---|---|---|
| Initial | 136.2 | 141.7 | 0.02 | 0.00 | 0.02 |
| 1M 40° C./75% RH | 129.9 | 136.9 | 0.05 | 0.07 | 0.18 |
| 6M 40° C./75% RH | 122.6 | 129.1 | 0.05 | 0.23 | 1.0 |
| 1M 25° C./60% RH | 133.7 | 139.9 | 0.04 | 0.07 | 0.18 |
| 6M 25° C./60% RH | 131.0 | 136.7 | 0.05 | 0.08 | 0.30 |
| Limits | 90-125% | 90-125% | NMT 0.2% | NMT 1.0% | NMT 2.0% |

*any value beyond 125% indicates overages added; Impurity A: trans-cholecalciferol

Example 3: Comparative Disintegration Characteristics of Vitamin $D_3$ Formulations of Examples 1 and 2

The disintegration time of vitamin $D_3$ formulations of Examples 1 and 2 were evaluated using a pharmacopeial disintegration tester according to the method described in section 2.9.1 of the European Pharmacopoeia 5.0. The time of disintegration of the tablets was noted and it was within the specified time limit of 30 minutes as is evident from the following Table 5. The disintegration time of formulations of example 1 and 2 above is less than the marketed product Cal D Forte®. Cal D Forte is a white, sugar-coated, biconvex tablet.

TABLE 5

Disintegration times of formulations of Examples 1 and 2

| | Formulation-Ex 1 | Formulation-Ex 2 | Cal D Forte |
|---|---|---|---|
| Disintegration Time | 6 min. 20 sec | 4 min. 30 sec | 15 min. 05 sec. |

Example 4: Comparative Evaluation of Chemical Stability of Formulations of Examples 1 and 2

The chemical stability of formulations 1 and 2 of the present invention was evaluated in amber colored glass vials for 1 month at 40° C./75% RH. Table 6 beneath indicates the assay and total % impurity for the two formulations. The 1M stability data of the formulations indicates that the formulations of Examples 1 and 2 of the present invention were more stable when compared to the marketed formulation.

TABLE 6

Chemical stability of Example 1 and 2 formulations compared to Cal D Forte.

| Formulation | Condition | Combined Assay* (%) (Vitamin $D_3$ + Precholecalciferol) | Impurity A (%) | Single max unspecified Impurity (%) | Total Impurity (%) |
|---|---|---|---|---|---|
| Formulation 1 | Initial | 124.4 | — | 0.06 | 0.10 |
|  | 1M 40° C./75% RH | 120.1 | — | 0.09 | 0.21 |
| Formulation 2 | Initial | 141.7 | 0.02 | 0.00 | 0.02 |
|  | 1M 40° C./75% RH | 136.9 | 0.05 | 0.07 | 0.18 |
| Cal D Forte ® | Initial | 79.9 | 0.28 | 44 | 45.05 |
|  | 1M 40° C./75% RH | 74.9 | 0.21 | 41 | 42.5 |
|  | Limits | 90-125% | NMT 0.2% | NMT 1% | NMT 2% |

*any value beyond 125% indicates overages added; Impurity A: trans-cholecalciferol Example 5: Formulation of Vitamin $D_3$ (50,000 IU)

A stabilized formulation of vitamin $D_3$ was prepared as per the following composition:

TABLE 7

Composition of Vitamin $D_3$ formulation

| Ingredients | mg/tablet |
|---|---|
| Vitamin $D_3$* | 122.5 |
| Calcium hydrogen phosphate dihydrate | 54.5 |
| Croscarmellose sodium | 20 |
| Colloidal anhydrous silica | 1 |
| Magnesium stearate | 2 |
| Coating | |
| Opadry II 85F18422 white | 6 |
| Opadry FX 63F97546 Silver | 4 |
| Total | 210 |

*Vitamin $D_3$ (50,000 IU + overages) incorporated is in the form of a commercially available blend consisting of vitamin $D_3$, hydrogenated castor oil, butylated hydroxyanisole and butylated hydroxytoluene.

Procedure

Vitamin $D_3$ commercially available as a blend was blended with calcium hydrogen phosphate dihydrate, croscarmellose sodium and colloidal anhydrous silica. This blend was further lubricated with magnesium stearate and finally compressed. The compressed tablets were then coated with Opadry II 85F18422 White and Opadry FX 63F97546 Silver to form a stabilized tablet formulation of vitamin $D_3$. The formulated tablets had a desirable disintegration time of less than 10 minutes.

Chemical Stability

The chemical stability of this formulation in amber colored glass bottle was evaluated for 3 months at 25° C./60% RH and 40° C./75% RH. Table 8 beneath indicates that the total unknown impurities were within limits during the study. Assay values also were found to be in trend with the initial assay values, indicating that the formulation was stable.

TABLE 8

Assessment of chemical stability

| Condition | Combined Assay (%) (Vitamin $D_3$ + Precholecalciferol) (%) | Total unknown impurity (%) |
|---|---|---|
| Initial | 98.22 | 0.28 |
| 1M 25° C./60% RH | 97.95 | 0.25 |
| 2M 25° C./60% RH | 97.82 | 0.34 |
| 3M 25° C./60% RH | 97.89 | 0.29 |
| 1M 40° C./75% RH | 96.65 | 0.27 |
| 2M 40° C./75% RH | 96.26 | 0.47 |
| 3M 40° C./75% RH | 95.67 | 0.45 |
| Limits | 90-125% | NMT 2.0% |

INDUSTRIAL APPLICABILITY

The stable solid formulations of vitamin $D_3$ of the invention, and processes for preparation of the same, have application in healthcare, and particularly in the pharmaceutical, nutraceutical, vitamin supplementation, and medical fields.

The invention claimed is:

1. A stable solid tablet formulation of vitamin $D_3$ comprising:
    (a) a tablet core comprising:
        i) about 1,000 IU to about 65,000 IU of vitamin $D_3$, about 7,000 IU of vitamin $D_3$, about 40,000 IU to about 65,000 IU of vitamin $D_3$, or about 50,000 IU of vitamin $D_3$,
        ii) at least one lipophilic dispersant,
        iii) one or more antioxidants,
        iv) at least one adsorbent, and
        v) one or more pharmaceutically acceptable excipients; and
    (b) at least one barrier coating;
        wherein the vitamin $D_3$ is substantially uniformly dispersed throughout the tablet core; and wherein the formulation comprises less than about 2% by weight of total impurities after 6 months at 40° C. and 75% relative humidity.

2. The formulation of claim 1 wherein the lipophilic dispersant is a wax, a fatty acid, a long chain monohydric alcohol, a fat or combinations thereof.

3. The formulation of claim 2 wherein the fatty acid is a hydrogenated vegetable oil.

4. The formulation of claim 3 wherein the hydrogenated vegetable oil is hydrogenated castor oil, hydrogenated palm oil, hydrogenated peanut oil, hydrogenated rapeseed oil, hydrogenated rice bran oil, hydrogenated soybean oil, hydrogenated cottonseed oil, hydrogenated sunflower oil, or mixtures thereof.

5. The formulation of claim 1 wherein the antioxidant is tocopherol, tocopherol acetate, tocopherol acid succinate, β-carotene, propyl gallate, butylated hydroxytoluene (BHT), butylated hydroxyanisole, vitamin E, ascorbic acid, sodium ascorbate, calcium ascorbate, ascorbic palmitate, 2,4,5-tri-hydroxybutyrophenone, 4-hydroxymethyl-2,6-di-tert-butyl-phenol, erythorbic acid, gum guaiac, thiodipropionic acid, dilauryl thiodipropionate, tertbutylhydroquinone or combinations thereof.

6. The formulation of claim 1 wherein the adsorbent is mannitol, dibasic calcium phosphate, dicalcium phosphate dihydrate, calcium hydrogen phosphate dihydrate, calcium phosphate tribasic, or combinations thereof.

7. The formulation of claim 1 wherein the pharmaceutically acceptable excipient is a diluent, binder, disintegrant, lubricant, colorant, coating agent, anti-adherent, glidant, or combinations thereof.

8. The formulation of claim 1 wherein the barrier coating comprises hydroxypropyl methylcellulose, polyvinyl alcohol, polyvinyl acetate, sodium carboxymethyl cellulose, pullulan, polyvinyl alcohol and vinyl alcohol-ethylene glycol copolymer; copolymer comprising methyl methacrylate and diethylaminoethyl methacrylate, poylmethacrylic acids, polymethacrylates or combinations thereof.

9. The formulation of claim 1 comprising:
(a)
   i) a tablet core comprising vitamin $D_3$, hydrogenated vegetable oil, butylated hydroxyanisole, mannitol, and magnesium stearate; and
   ii) a barrier coating, or
(b)
   i) a tablet core comprising vitamin $D_3$, hydrogenated castor oil, butylated hydroxyanisole, butylated hydroxytoluene, dicalcium phosphate dehydrate, croscarmellose sodium, and magnesium stearate; and
   ii) a barrier coating, or
(c)
   i) a tablet core comprising vitamin $D_3$, hydrogenated castor oil, butylated hydroxyanisole, butylated hydroxytoluene, dicalcium phosphate dehydrate, croscarmellose sodium, colloidal anhydrous silica, and magnesium stearate; and
   ii) a barrier coating.

10. The formulation of claim 1 wherein the formulation is in the form of a monolithic tablet dosage form.

11. The formulation of claim 1 wherein the formulation comprises vitamin $D_3$ in an amount of (a) about 0.01% to about 25% by weight of the composition,
(b) about 0.1% to about 20% by weight of the composition, or
(c) about 0.3% to about 20% by weight of the composition.

12. The formulation of claim 1 wherein the ratio of lipophilic dispersant to the vitamin $D_3$ is not more than about 85.

13. The formulation of claim 1 wherein the vitamin $D_3$ in the formulation is stable for at least about six months at 25° C. and 60% relative humidity as determined by HPLC analysis.

14. The formulation of claim 13 wherein the formulation retains after at least about six months at 25° C. and 60% relative humidity at least 90%, at least 95% or at least 98% of the vitamin $D_3$ initially present in the formulation as determined by HPLC analysis.

15. The formulation of claim 1 wherein the tablet core comprises
(a)
   i) granules comprising vitamin $D_3$, at least one lipophilic dispersant, one or more antioxidants and optionally one or more pharmaceutically acceptable excipients;
   ii) at least one adsorbent; and
   iii) one or more pharmaceutically acceptable excipients; or
(b)
   i) granules comprising vitamin $D_3$, at least one lipophilic dispersant, one or more antioxidants, at least one adsorbent and optionally one or more pharmaceutically acceptable excipients;
   ii) at least one adsorbent; and
   iii) one or more pharmaceutically acceptable excipients.

16. A process of preparing the formulation of claim 1 comprising:
(a) blending a vitamin $D_3$ blend containing a lipophilic dispersant and an antioxidant with at least one adsorbent,
(b) lubricating the blend of (a),
(c) compressing the lubricated blend of (b) into tablets; and
(d) coating the compressed tablets of (c) with at least one barrier coating.

17. A method of treating or preventing conditions associated with vitamin $D_3$ insufficiency or deficiency by administering to a subject in need thereof the formulation of claim 1.

18. The method of claim 17 wherein the condition associated with vitamin $D_3$ insufficiency or deficiency is osteomalacia, osteoporosis, osteopenia, fibrogenesis imperfecta ossium, rickets or hypocalcaemia.

19. A process of claim 16 wherein the blend is prepared by dissolving at least one antioxidant in a suitable solvent, dissolving vitamin $D_3$ in the solution of (a), melting the lipophilic dispersant, adding the solution of (b) into the melted dispersant of (c), incorporating a partial or complete amount of at least one adsorbent in the melted mass of (d) followed by cooling the mixture, sizing the cooled mass of (e) and sifting to obtain granules, blending the granules of (f) with the remaining pharmaceutically acceptable excipients and partial amount of the adsorbent, if any.

* * * * *